United States Patent [19]
Sommer

[11] Patent Number: 6,040,292
[45] Date of Patent: Mar. 21, 2000

[54] METHODS FOR TREATING DIABETES

[75] Inventor: Andreas Sommer, Danville, Calif.

[73] Assignee: Celtrix Pharmaceuticals, Inc., San Jose, Calif.

[21] Appl. No.: 09/326,189

[22] Filed: Jun. 4, 1999

[51] Int. Cl.⁷ ................................................. A61K 38/00
[52] U.S. Cl. ........................................................ 514/12
[58] Field of Search ............................................ 514/12

[56] References Cited

U.S. PATENT DOCUMENTS

| | | | |
|---|---|---|---|
| 4,988,675 | 1/1991 | Froesch et al. | 514/4 |
| 5,407,913 | 4/1995 | Sommer et al. | |
| 5,466,670 | 11/1995 | Dunger et al. | 514/12 |
| 5,527,776 | 6/1996 | Carlino et al. | |
| 5,674,845 | 10/1997 | MacCuish | 514/12 |
| 5,681,818 | 10/1997 | Spencer et al. | |
| 5,686,408 | 11/1997 | Moses et al. | 514/3 |
| 5,723,441 | 9/1998 | Higley et al. | |

FOREIGN PATENT DOCUMENTS

| | | |
|---|---|---|
| WO 95/03817 | 2/1995 | WIPO. |
| WO 95/04076 | 2/1995 | WIPO. |
| WO 95/13823 | 5/1995 | WIPO. |
| WO 96/02565 | 2/1996 | WIPO. |

OTHER PUBLICATIONS

Blum et al., 1991, "Plasma IGFBP–3 Levels as Clinical Indicators "in *Modern Concepts in Insulin–Like Growth Factors*, E.M. Spencer, ed., Elsevier, New York, pp. 381–393.

Clark et al., 1993, "Insulin–like Growth Factor–I Stimulation of Lymphopoiesus "*J. Clin. Invest.*92:540–548.

Clemmons et al., 1994, "Uses of Human Insulin–like Growth Factor–1 in Clinical Conditions "*J. Clin. Endocrinol. Metabol.*79(1):4–6.

Delany et al., 1994, "Cellular and Clinical Perspectives on Skeletal Insulin–like Growth Factor I "*J. Cell. Biochem.* 55:328–333.

Guler et aL., 1987, "Short–term Metabolic Effects of Recombinant Human Insulin–like Growth Factor I in Healthy Adults", *New England J. Med.* 317(3):137–140.

Lewis et al., 1993, "Insulin–like Growth Factor I: Potential for Treatment of Motor Neuronal Disorders "*Exp. Neurol.* 124:73–88.

Lieberman et al., 1992, "Effects of Recombinant Human Insulin–like Growth Factor–I (rhIGF–I) on Total and Free IGF–I Concentrations, IGF–Binding Proteins, and Glycemic Response in Humans", *J. Clin. Endocrinol. Metab.* 75(1):30–36.

Radulescu, Razvan T., 1994, *Trends Biochem Sci.* 19(7):278.

Sommer et al., 1991, "Molecular Genetics and Actions of Recombinant Insulin–Like Growth Factor Binding Protein–3", in *Modem Concepts of Insulin–Like Growth Factors*, E.M. Spencer, ed., Elsevier, New York, pp. 715–728.

Steenfos, Henrik H., 1994, "Growth Factors and Wound Healing "*Scand. J. Plast. Reconstr. Hand Surg.* 28:95–105.

Zapf et al., 1994, "Intravenously Injected Insulin–like Growth Factor (IGF) I/IGF Binding Protein–3 Complex Exerts Insulin–like Effects in Hypophysectomized, but Not in Normal Rats", *J. Clin. Invest.* 95:179–186.

*Primary Examiner*—Raymond Henley, III
*Attorney, Agent, or Firm*—Morrison & Foerster LLP

[57] ABSTRACT

The invention provides new methods for the treatment of diabetes mellitus, including type I, type II, and insulin resistant diabetes (both type I and type II). The methods of the invention employ administration of rhIGF-I/IGFBP-3 complex to a subject suffering from the symptoms of diabetes mellitus. Administration of rhIGF-I/IGFBP-3 to a subject suffering from the symptoms of diabetes mellitus results in amelioration or stabilization of the symptoms of diabetes.

14 Claims, No Drawings

METHODS FOR TREATING DIABETES

TECHNICAL FIELD

The invention relates to the field of medicine, in particular the treatment of the symptoms of diabetes mellitus by administration of insulin-like growth factor I complexed to insulin-like growth factor binding protein-3 (IGF-I/IGFBP-3 complex).

BACKGROUND ART

Diabetes mellitus is a syndrome with interrelated metabolic, vascular, and neuropathic components. The metabolic syndrome, generally characterized by hyperglycemia, comprises alterations in carbohydrate, fat and protein metabolism caused by absent or markedly reduced insulin secretion and/or ineffective insulin action. The vascular syndrome consists of abnormalities in the blood vessels leading to cardiovascular, retinal and renal complications. Abnormalities in the peripheral and autonomic nervous systems are also part of the diabetic syndrome.

Growth factors are polypeptides which stimulate a wide variety of biological responses (e.g., DNA synthesis, cell division, expression of specific genes, etc.) in a defined population of target cells. A variety of growth factors have been identified, including the transforming growth factor beta (TGF-β) superfamily, which includes the TGF-βs (1–5 and others) as well as bone morphogenetic proteins (BMPs), activins, inhibins, and the like, epidermal growth factor (EGF), platelet-derived growth factor (PDGF), fibroblast growth factor (FGF), insulin-like growth factor-I (IGF-1) and IGF-II.

IGF-I and IGF-II are related in amino acid sequence and structure, with each polypeptide having a molecular weight of approximately 7.5 kilodaltons (kD). IGF-I mediates the major effects of growth hormone, and thus is the primary mediator of growth after birth. Both IGF-I and IGF-II have insulin-like activities (hence their names), and are mitogenic (stimulate cell division) for the cells in neural tissue, muscle, reproductive tissue, skeletal tissue and a wide variety of other tissues. Unlike most growth factors, the IGFs are present in substantial quantity in the circulation, but only a very small fraction of this IGF is free in the circulation or in other body fluids. Most circulating IGF is bound to an IGF-binding protein called IGFBP-3.

Almost all IGF circulates in a non-covalently associated ternary complex composed of IGF-I or IGF-II, IGFBP-3, and a larger protein subunit termed the acid labile subunit (ALS). This ternary complex is composed of equimolar amounts of each of the three components. ALS has no direct IGF binding activity and appears to bind only to the IGF/IGFBP-3 binary complex. The ternary complex of IGF+IGFBP-3+ALS has a molecular weight of approximately 150 Kd. This ternary complex is alleged to function in the circulation "as a reservoir and a buffer for IGF-I and IGF-II preventing rapid changes in the concentration of free IGF" (Blum et al., 1991, "Plasma IGFBP-3 Levels as Clinical Indicators" in *Modem Concepts in Insulin-Like Growth Factors*, E. M. Spencer, ed., Elsevier, N.Y., pp. 381–393). The ternary complex is also believed to play an important role in the prevention of hypoglycemia due to high doses of IGF-I, by binding IGF-I/IGFBP-3 complex and restricting its distribution (Zapf et al., 1994, "Intravenously Injected Insulin-like Growth Factor (IGF) I/IGF Binding Protein-3 Complex Exerts Insulin-like Effects in Hypophysectomized, but Not in Normal Rats", *Clinical Investigation* 95:179–186).

Nearly all of the IGF-I, IGF-II and IGFBP-3 in the circulation is in complexes, so very little free IGF is detectable. Moreover, a high level of free IGF in blood is generally considered undesirable. The most commonly cited side effect of IGF-I administration is the induction of clinically significant hypoglycemia. IGF-I induces significant hypoglycemia (significant hypoglycemia is normally defined as a decrease in blood glucose of 30% or more) in humans at doses of 30 μg/kg by intravenous administration and 100 μg/kg by subcutaneous administration (Lieberman et al., 1992, "Effects of Recombinant Human Insulin-like Growth Factor-I (rhIGF-I) on Total and Free IGF-I Concentrations, IGF-Binding Proteins, and Glycemic Response in Humans", *J. Clin. Endocrinol. Metab.* 75(1):30–36; Guler et al., 1987, "Short-term Metabolic Effects of Recombinant Human Insulin-like Growth Factor I in Healthy Adults", *New England J. Med.* 317(3):137–140). Other frequently observed significant side effects of free IGF-I administration include edema, jaw pain, and hypophosphatemia.

Studies with IGF-I have suggested its utility in treating a wide variety of indications. Clemmons and Underwood (1994, "Uses of Human Insulin-like Growth Factor-I in Clinical Conditions" *J. Clin. Endocrinol. Metabol.* 79(1):4–6) have suggested that IGF-I may be useful for the treatment of catabolic states, such as can arise due to trauma, severe burns, and major surgery. Clemmons and Underwood (supra) also suggest the utility of IGF-I in the treatment of acute and chronic renal disorders. IGF-I may be useful for the treatment of lymphopoietic disorders (Clark et al., 1993, "Insulin-like Growth Factor I Stimulation of Lymphopoiesis" *J. Clin. Invest.* 92:540–548). IGF-I has also been suggested as potentially useful in the treatment of bone disorders, such as osteoporosis, as well as wound healing and peripheral nerve disorders (Delany et al., 1994, "Cellular and Clinical Perspectives on Skeletal Insulin-like Growth Factor I" *J. Cell. Biochem.* 55(3):328–333; Steenfos, 1994, "Growth Factors and Wound Healing" Scand *J. Plast. Reconstr. Surg. Hand Surg.* 28(2):95–105; Lewis et al., 1993, "Insulin-like Growth Factor I: Potential for Treatment of Motor Neuronal Disorders" *Exp. Neurol.* 124(1):73–88).

Because of its insulin-like effects (especially the induction of hypoglycemia), IGF-I has been studied for the treatment of diabetes, both type I juvenile, or insulin-dependent) and type II (adult, or insulin independent), as well as for the treatment of insulin resistance in both type I and type II diabetes.

U.S. Pat. No. 5,674,845 teaches the use of IGF-I for the treatment of type A diabetes, a rare form of insulin-resistant diabetes. U.S. Pat. No. 4,988,675 teaches the use of IGF-I, alone or in combination with insulin, for the type I and type II diabetics with insulin resistance. U.S. Pat. No. 5,466,670 teaches the use of IGF-I for the treatment of type I diabetes. None of these patents teaches or suggests the use of IGF-I/IGFBP-3 complex for the treatment of diabetes of any type.

U.S. Pat. No. 5,686,408 teaches the administration IGF-I in accordance with a particular dosing regimen for the treatment of insulin resistance. This patent teaches that IGF-I/IGFBP-3 complex would be disadvantageous for the treatment of diabetes, because IGFBP's have been shown to decrease the hypoglycemic and other side effects of IGF-I. Since it is well known to those skilled in the art that IGF-I, when complexed with IGFBP-3, no longer causes hypoglycemia, hypophosphatemia, edema or jaw pain, it would be expected that IGF-I/IGFBP-3 complex would not be able to lower insulin requirements in a manner similar to free IGF-I.

Administration of IGF-I/IGFBP-3 complex has been suggested for a number of different indications, including wound healing (Sommer et al., 1991, "Molecular Genetics and Action of Recombinant Insulin-Like Growth Factor Binding Protein-3", in *Modem Concepts of Insulin-Like Growth Factors*, E.M. Spencer, ed., Elsevier, N.Y., pp. 715–728; U.S. Pat. No. 5,407,913), osteoporosis and other bone disorders (U.S. Pat. No. 5,681,818 and International Patent Application No. WO 96/02565), and disorders of the ophthalmic, neural, renal, reproductive, hematopoietic and immune systems (see U.S. patent application Ser. No. 08/008,915, International Patent Applications Nos. WO 95/13823 and WO 95/03817 and U.S. Pat. Nos. 5,723,441 and 5,527,776).

There remains a need in the art for effective treatments for diabetes without inducing undesirable side effects.

DISCLOSURE OF THE INVENTION

The invention provides new treatments for diabetes mellitus. In the methods of the invention, IGF-I/IGFBP-3 complex is administered to subjects suffering from type I diabetes (IDDM), type II diabetes (NIDDM), and insulin resistant type I or type II diabetes and Type A insulin resistance. Administration of IGF-I/IGFBP-3 complex results in lowered serum glucose and, in patients receiving exogenous insulin, reduced need for exogenous insulin.

In one aspect, the invention provides new methods for treatment of diabetes mellitus by administering an effective amount of IGF-I/IGFBP-3 complex to a subject suffering from symptoms or complications of diabetes mellitus. The diabetes mellitus may be type I, type II, gestational or insulin resistant (type I, type II, or type A) diabetes. Administration may be on a continuous or discontinuous schedule.

In another aspect, the invention provides kits for the treatment of diabetes mellitus. The kits of the invention comprise a package of IGF-I/IGFBP-3 complex and instructions for the use of IGF-I/IGFBP-3 complex in the treatment of diabetes.

BEST MODE FOR CARRYING OUT THE INVENTION

IGF-I has well known hypoglycemic effects, which are largely the basis of the use of IGF-I for the treatment of diabetes. Complexing IGF-I to IGFBP-3 has been shown to inhibit hypoglycemia induced by IGF-I administration. However, applicants have found that administration of IGF-I/IGFBP-3 complex results in effective treatment of the symptoms of diabetes mellitus, despite the presence of IGFBP-3, which blocks the induction of hypoglycemia by IGF-I at all but the highest doses. Additionally, administration of IGF-I as IGF-I/IGFBP-3 complex eliminates or reduces other IGF-I associated adverse effects, such as edema, jaw pain, and hypophosphatemia.

The invention relates to the treatment of the symptoms of diabetes mellitus, including type I diabetes (IDDM), type II diabetes (NIDDM), and insulin resistance in both types of diabetes mellitus, and Type A insulin resistance, by administering a complex of IGF-I and IGFBP-3 (IGF-I/IGFBP-3 complex) to a subject suffering from the symptoms of diabetes. Applicants have found that administration IGF-I/IGFBP-3 complex to subjects with diabetes mellitus ameliorates the symptoms of diabetes mellitus.

The invention also provides kits relating to the treatment of diabetes. The kits of the invention comprise IGF-I/IGFBP-3 complex, preferably recombinant human IGF-I/IGFBP-3 complex with instructions for the use of the complex for the treatment of diabetes.

Definitions

As used herein, "IGF-I" refers to insulin-like growth factor I from any species, including bovine, ovine, porcine and human, in native sequence or variant form, including but not limited to naturally-occurring allelic variants, and from any source, whether natural, synthetic or recombinant, provided that it will bind IGFBP-3. Preferred herein is human native-sequence, mature IGF-I, more preferably without an amino-terminal methionine. More preferably, the native sequence, mature IGF-I is produced recombinantly, for example, as described in PCT publication WO 95/04076.

As used herein, "acid labile subunit" and "ALS" refer to the acid labile, 84–86 kD, non-IGF-binding subunit of the 125–150 kD ternary complex. ALS is preferably human ALS. ALS may be from any source, including natural, synthetic, or recombinant sources.

"Insulin-like growth factor binding protein 3" (IGFBP-3) is a member of the insulin-like growth factor binding protein family. IGFBP-3 may be from any species, including bovine, ovine, porcine and human, in native sequence or variant form, including but not limited to naturally-occurring allelic variants (e.g., having either an alanine or a glycine at position 5 of the mature protein). Preferred IGFBP-3 embodiments include native sequence human IGFBP-3 and variants of human IGFBP-3 wherein the one or more of the asparagine residues which form the normal N-linked glycosylation sites (positions 89, 109 and 172) are changed to aspartate (e.g.: N89D; N109D; N172D; N89D,N109D; N89D,N172D; N109D,N172D; and N89D,N109D,N172D variants) or to other amino acid residues (e.g: N89X; N109X; N172X; N89X,N109X; N89X,N172X; N109X, N172X; and N89X,N109X,N172X variants) as well as variants which have been altered to improve resistance to degradation, such as alterations at positions 116 and 135 (e.g., D116E, D135E and D116E,D135E), or alterations which affect the nuclear localization signal (NLS) of IGFBP-3, which is located at residues 215 through 232 (Radulescu, 1994, *Trends Biochem Sci.* 19(7):278). Examples of preferred NLS variant IGFBP-3s include K228E, R230G, K228E,R230G, K228X, R230X, and K228X,R230X, as well as variations at residues 215, 216 and 231. Of course, a variant IGFBP-3 may include more than one type of variation (e.g., a variant IGFBP-3 may be both ND variant and degradation resistant variant). IGFBP-3 can form a binary complex with IGF, and a ternary complex with IGF and the acid labile subunit (ALS). IGFBP-3 may be from any source, whether natural, synthetic or recombinant, provided that it will bind IGFI and ALS. Preferably, IGFBP-3 is produced recombinantly, as described in PCT publication WO 95/04076.

As used herein, "treatment" is an approach for obtaining beneficial or desired clinical results. Desired clinical results include (a) increase in insulin sensitivity (b) reduction in insulin dosing while maintaining glycemic control (c) decrease in HbA1c (d) improved glycemic control (e) reduced vascular, renal, neural, retinal, and other diabetic complications (f) prevention or reduction of "dawn phenomenon" (g) improved lipid profile (h) reduced complications of pregnancy, and (h) reduced ketoacidosis. For purposes of this invention, beneficial or desired clinical results include, but are not limited to, alleviation of symptoms associated with diabetes, diminishment of the extent of the symptoms of diabetes, stabilization (i.e. not worsening) of the symptoms of diabetes (e.g., reduction of insulin requirement), and delay or slowing of diabetes progression. As will be understood by one of skill in the art, the particular symptoms which yield to treatment in accordance with the invention will depend on the type of diabetes being treated.

A "therapeutic composition", as used herein, is defined as comprising IGF-I complexed with its binding protein, IGFBP-3 (IGF-I/IGFBP-3 complex). The therapeutic composition may also contain other substances such as water, minerals, carriers such as proteins, and other excipients known to one skilled in the art.

As used herein, "symptoms and complications of diabetes" are defined as hyperglycemia, unsatisfactory glycemic control, ketoacidosis, insulin resistance, elevated growth hormone levels, elevated levels of glycosylated hemoglobin and advanced glycosylation end-products (AGE), dawn phenomenon, unsatisfactory lipid profile, vascular disease (e.g., atherosclerosis), microvascular disease, retinal disorders (e.g., proliferative diabetic retinopathy), renal disorders, neuropathy, complications of pregnancy (e.g., premature termination and birth defects) and the like.

As used herein, the term "comprising" and its cognates are used in their inclusive sense; that is, equivalent to the term "including" and its corresponding cognates.

The method of the invention involves giving a dose of IGF-I/GFBP-3 complex to a subject suffering from diabetes mellitus, particularly type I diabetes (IDDM), type II diabetes (NIDDM), and insulin resistant diabetes (including type I and type II insulin resistant diabetes, and Type A insulin resistance).

Diabetes mellitus is a relatively common disorder (estimated at about 1% prevalence in the general population) which is characterized by hyperglycemia. There are three basic types of diabetes mellitus, type I or insulin-dependent diabetes mellitus (IDDM), type II or non-insulin-dependent diabetes mellitus (NIDDM), and type A insulin resistance, although type A is relatively rare. Patients with either type I or type II diabetes can become insensitive to the effects of exogenous insulin ("insulin resistant") through a variety of mechanisms. Type A insulin resistance results from either mutations in the insulin receptor gene or defects in post-receptor sites of action critical for glucose metabolism. Diabetes is generally controlled through administration of exogenous insulin (especially in type I diabetics), dietary control and exercise (especially in type II diabetics) or both. Diabetic subjects can be easily recognized by the physician, and are characterized by hyperglycemia, impaired glucose tolerance, glycosylated hemoglobin and, in some instances, ketoacidosis associated with trauma or illness.

Preferably, the IGF-I and IGFBP-3 used to form IGF-I/IGFBP-3 complex for use in the methods of the invention are "species matched" (i.e., the IGF-I and IGFBP-3 are from the same species as the subject to which they are administered). Accordingly, where a human is the subject, the IGF-I and IGFBP-3 used to form the complex are preferably human IGF-I and IGFBP-3. More preferably, the IGF-I and IGFBP-3 used to form the complex are recombinant proteins, although IGF-I and/or IGFBP-3 derived from natural sources are also acceptable.

Preferably, the IGF-I/IGFBP-3 complex is administered by parenteral route of administration such as, but not limited to, intravenous (IV), intramuscular (IM), subcutaneous (SC), intraperitoneal (IP), transdermal, intranasal, and inhalant routes. IV, IM, SC, and IP administration may be by bolus or infusion, and in the case of SC, may also be by slow release implantable device, including, but not limited to pumps, slow release formulations, and mechanical devices. One preferred method for administration of IGF-I/IGFBP-3 complex is by subcutaneous infusion, particularly using a metered infusion device, such as a pump.

The formulation, route and method of administration, and dosage will depend on the medical history of the patient, including the severity of the diabetes and/or insulin resistance. In general, a dose that is administered by subcutaneous injection will be greater than the therapeutically-equivalent dose given intravenously or intramuscularly. A composition comprising equimolar amounts of IGF-I and IGFBP-3 is preferred. Preferably the IGF-I and IGFBP-3 are complexed prior to administration. Preferably, the complex is formed by mixing approximately equimolar amounts of IGF-I and IGFBP-3 dissolved in physiologically compatible carriers such as normal saline, or phosphate buffered saline solution. Most preferably, a concentrated solution of rhIGF-I and a concentrated solution of rhIGFBP-3 are mixed together for a sufficient time to form an equimolar complex.

For parenteral administration, compositions of the complex may be semi-solid or liquid preparations, such as liquids, suspensions, and the like. Physiologically compatible carriers include, but are not limited to, normal saline, serum albumin, 5% dextrose, plasma preparations, and other protein-containing solutions. For intranasal and inhalant administration, a powdered formulation (such as a freeze-dried powder) may be useful. Optionally, the carrier may also include anti-microbial agents, preservatives, detergents or surfactants.

The dose of complex to be administered can be readily determined by those skilled in the art, based on the condition to be treated, the severity of the condition, and the patient's medical history. Preferably, when the complex is administered daily, the intravenous or intramuscular dose for a human is about 0.3 mg/kg to 10 mg/kg of body weight per day. More preferably, the daily intravenous or intramuscular dose for a human is about 0.5 mg/kg to 5 mg/kg. Most preferably, the daily intravenous or intramuscular dose for a human is about 0.5 mg/kg to 3 mg/kg. For subcutaneous administration, the dose is preferably greater than the therapeutically-equivalent dose given intravenously. Preferably, the daily subcutaneous dose for a human is 0.3 mg/kg to 20 mg/kg, more preferably 0.5 mg/kg to 5 mg/kg or about 0.5 mg/kg to 3 mg/kg.

The invention contemplates a variety of dosing schedules. The invention encompasses continuous dosing schedules, in which rhIGF-I/IGFBP-3 is administered on a regular (daily, weekly, or monthly, depending on the dose and dosage form) basis without substantial breaks. Preferred continuous dosing schedules include daily continuous infusion, where rhIGF-I/IGFBP-3 is infused each day, and continuous bolus administration schedules, where IGF-I/IGFBP-3 is administered at least once per day by bolus injection or inhalant or intranasal routes. Continuous administration schedules are preferably for at least 2, 3, 4, 5, 6, or 7 days, 1, 2, 3, 4, 5, or 6 weeks, or at least any combination thereof. The invention also encompasses discontinuous dosing schedules. The exact parameters of discontinuous administration schedules will vary according the formulation, method of delivery and the clinical needs of the subject. For example, if the IGF-I/IGFBP-3 complex is administered by infusion, administration schedules (or "cycles") comprising a first period of administration (an "on period") followed by a second period in which IGF-I/IGFBP-3 is not administered (an "off period") which is greater than, equal to, or less than the on period. Examples of discontinuous administration schedules for infusion administration include schedules comprising on periods selected from 1, 2, 3, 4, 5, 6, or 7 days, 1, 2, 3, 4, or more weeks, or any combination thereof, and off periods selected from 1, 2, 3, 4, 5, 6, or 7 days, 1, 2, 3, 4, or more weeks.

Where the administration is by bolus injection, especially bolus injection of a slow release formulation, dosing schedules may also be continuous in that IGF-I/IGFBP-3 is administered each day, or may be discontinuous. Discontinuous bolus injection dosing schedules, for example, include on periods (days on which an injection is given) selected from 1, 2, 3, 4, 5, 6, or 7 days, 1, 2, 3, 4, or more weeks, or any combination thereof, and off periods (days on which an injection is not given) selected from 1, 2, 3, 4, 5, 6, or 7 days, 1, 2, 3, 4, or more weeks.

As will be apparent to ore of skill in the art, intranasal and inhalant administration is generally more convenient for the subject as it does not involve the use of injections, catheters, or transdermal infusion devices. Intranasal and inhaled doses may thus be smaller, but given more frequently, than doses given by other parenteral routes. Accordingly, intranasal and inhalant dosing schedules may include a single dose per "on" day, or may involve multiple doses (e.g., 2, 3, 4, 5 or more doses per day). Dosing schedules may be continuous or discontinuous, with discontinuous schedules utilizing on periods (e.g., days on which IGF-I/IGFBP-3 is administered at least once) selected from 1, 2, 3, 4, 5, 6, or 7 days, 1, 2, 3, 4, or more weeks, or any combination thereof, and off periods (e.g., days on which IGF-I/IGFBP-3 is not administered) selected from 1, 2, 3, 4, 5, 6, or 7 days, 1, 2, 3, 4, or more weeks.

Continuous and discontinuous administration schedules by any method also include dosing schedules in which the dose is modulated throughout the "on" period, such that, for example, at the beginning of the on period, the dose is low and increased until the end of the on period, the dose is initially high and decreased during the on period, the dose is initially low, increased to a peak level, then reduced towards the end of the on period, and any combination thereof.

The effects of administration of rhIGF-I/IGFBP-3 can be measured by a variety of assays known in the art. Most commonly, alleviation of the effects of diabetes will result improved glycemic control (as measured by serial testing of blood glucose), reduction in the requirement for insulin to maintain good glycemic control, reduction in serum insulin levels, reduction in glycosylated hemoglobin, reduction in blood levels of advanced glycosylation end-products (AGE), reduced "dawn phenomenon", reduced ketoacidosis, and improved lipid profile. Alternately, administration of rhIGF-I/IGFBP-3 can result in a stabilization of the symptoms of diabetes, as indicated by reduction of blood glucose levels, reduced insulin requirement, reduced serum insulin levels, reduced glycosylated hemoglobin and blood AGE, reduced vascular, renal, neural and retinal complications, reduced complications of pregnancy, and improved lipid profile.

The invention also provides kits for the treatment of diabetes mellitus (type I and type II and type I, type II and type A insulin resistant diabetes mellitus). The kits of the invention comprise one or more packages of IGF-I/IGFBP-3 in combination with a set of instructions, generally written instructions, relating to the use and dosage of IGF-I/IGFBP-3 for the treatment of diabetes. The instructions included with the kit generally include information as to dosage, dosing schedule, and route of administration for the treatment of diabetes. The packages of IGF-I/IGFBP-3 may be unit doses, bulk packages (e.g., multi-dose packages) or sub-unit doses.

IGF-I/IGFBP-3 may be packaged in any convenient, appropriate packaging. For example, if the IGF-I/IGFBP-3 is a freeze-dried formulation, an ampoule with a resilient stopper is normally used, so that the drug may be easily reconstituted by injecting fluid through the resilient stopper. Ampoules with non-resilient, removable closures (e.g., sealed glass) or resilient stoppers are most conveniently used for injectable forms of IGF-I/IGFBP-3. Also contemplated are packages for use in combination with a specific device, such as an inhaler, nasal administration device (e.g., an atomizer) or an infusion device such as a minipump.

EXAMPLES

Example 1

Treatment of Type 1 Diabetes Mellitus with IGF-I/IGFBP-3 Complex

Administration of recombinant human IGF-I/IGFBP-3 (rhIGF-I/IGFBP-3) was tested in Type I diabetics. A double-blinded, placebo-controlled, multi-center study was conducted with 12 subjects aged 19–47 years (mean=32 years). The study utilized a cross-over design, which allowed each subject to serve as his or her own control Upon entry into the study, each subject was randomly assigned to one of two groups, then "run in" to the study for a 2–3 week period. During the run in period, the subjects were placed on their normal, weight maintaining diet, with the aim of maintaining each subject's weight throughout the study. Subjects were asked to complete a food diary, so that diet could be adjusted if weight loss was observed. Each subject's glucose was monitored and insulin was adjusted so as to maintain his or her normal level of glycemic control during the run in period.

After completion of the run in period, the subjects were admitted to an in-patient study facility for a "model day" study. During the model day study, serum glucose and insulin were measured every two hours, with additional samples at 30 minute intervals for two hours after meals or snacks. Blood samples were drawn and a number of parameters, including fasting hemoglobin A1C and fructosamine, IGF-I, IGFBP-2 and IGFBP-3 were measured.

The morning following the model day study, the subjects began cycle one of the study. Subjects in group 1 received rhIGF-I/IGFBP-3 (2 mg/kg/day in 105 mM sodium chloride, 50 mM sodium acetate, pH 5.5) as the test article by continuous subcutaneous infusion using a mini pump. Subjects in group 2 received placebo (105 mM sodium chloride, 50 mM sodium acetate, pH 5.5) as the test article, also by continuous subcutaneous infusion. All subjects were discharged from the in-patient unit a day after initiation of cycle one, and continued administration of the test article for two weeks. During the 2-week treatment period, subjects monitored their glucose levels and adjusted their insulin intake accordingly. On the final day of administration, the subjects were readmitted to the in-patient unit to undergo a repeat of the model day study.

After discharge from the in-patient model day study, the subjects were given a 2–3 week "washout" period, during which they were instructed to monitor blood glucose at least four times daily and maintain normal glycemic control with injected insulin.

At the end of the washout period, the subjects returned to the in-patient unit, where the model day study was repeated a third time, and the subjects entered into cycle two of the study, which was identical to cycle one, except that the test articles were reversed (e.g., group 1 subjects received placebo and group 2 subjects received rhIGF-I/IGFBP-3). Cycle two was concluded with readmission to the in-patient unit and a repeat of the model day study. rhIGF-I/IGFBP-3 treatment decreased 24-hour insulin requirements by 49% (27.3±12.8 vs. 53.6±18.7 U/24 hr; p<0.001) and reduced mean home glucose values by 23% (144±73 vs. 187±95 mg/dL; p<0.02). All patients receiving rhIGF-I/IGFBP-3 noted a decrease in insulin requirements. The accuracy of the insulin diaries submitted by the patients was confirmed by measuring free insulin in the blood circulation, which was reduced 47% (20.1±9.0 vs. 37.5±15.9) in patients receiving rhIGF-I/IGFBP-3. Growth hormone, known to substantially contribute to insulin resistance, was reduced by 77% in patients receiving rhIGF-I/IGFBP-3 (0.55±0.23 vs. 2.48±0.73).

No significant drug-related side effects were observed. Subjects did not experience edema, jaw pain, or headache-side-effects almost invariably observed when human subjects are treated with substantial doses of free IGF-I. rhIGF-I/IGFBP-3 produced the desirable biological effects of IGF-I in diabetic subjects, but with a surprising lack of side effects.

The patents, patent applications, and publications cited throughout the disclosure are incorporated herein by reference in their entirety.

The present invention has been detailed both by direct description and by example. Equivalents and modifications of the present invention will be apparent to those skilled in the art, and are encompassed within the scope of the invention.

I claim:

1. A method for treatment of diabetes mellitus, comprising:
   administering an effective amount of IGF-I/IGFBP-3 complex to a subject suffering from symptoms or complications of diabetes mellitus.

2. The method of claim 1 wherein said IGF-I/IGFBP-3 complex is human IGF-I/IGFBP-3 complex.

3. The method of claim 2 wherein said IGF-I/IGFBP-3 complex is recombinant human IGF-I/IGFBP-3 complex.

4. The method of claim 1 wherein said diabetes mellitus is type I diabetes mellitus.

5. The method of claim 4 wherein said type I diabetes mellitus is insulin resistant type I diabetes mellitus.

6. The method of claim 1 wherein said diabetes mellitus is type II diabetes mellitus.

7. The method of claim 6 wherein said type II diabetes mellitus is insulin resistant type II diabetes mellitus.

8. The method of claim 1 wherein said diabetes mellitus is type A insulin resistance diabetes mellitus.

9. The method of claim 1 wherein said IGF-I/IGFBP-3 complex is administered on a continuous administration schedule.

10. The method of claim 1 wherein said IGF-I/IGFBP-3 complex is administered on a discontinuous administration schedule comprising cycles which include an on period wherein IGF-I/IGFBP-3 complex is administered and an off period wherein IGF-I/IGFBP-3 complex is not administered.

11. The method of claim 10 wherein said off period is less than said on period.

12. The method of claim 10 wherein said off period is greater than said on period.

13. The method of claim 10 wherein said off period is equal to said on period.

14. A kit, comprising
   a package comprising IGF-I/IGFBP-3 complex; and
   instructions for use of said IGF-I/IGFBP-3 complex for the treatment of diabetes.

* * * * *